United States Patent [19]

Yellin et al.

[11] Patent Number: 4,464,374

[45] Date of Patent: Aug. 7, 1984

[54] SUBSTITUTED GUANIDINE DERIVATIVES, PROCESSES, PHARMACEUTICAL COMPOSITIONS AND METHODS AND INTERMEDIATES

[75] Inventors: Tobias O. Yellin, Fremont, Calif.; David J. Gilman, Tytherington, England; Derrick F. Jones, Tytherington, England; Keith Oldham, Cheadle, England

[73] Assignees: ICI Americas Inc., Wilmington, Del.; Imperial Chemical Industries PLC, London, England

[21] Appl. No.: 286,064

[22] Filed: Jul. 23, 1981

[30] Foreign Application Priority Data

Jul. 30, 1980 [GB] United Kingdom ................ 8024963

[51] Int. Cl.³ ................ C07D 277/38; C07D 239/42; A61K 31/425; A61K 31/505
[52] U.S. Cl. ................ 424/251; 544/194; 544/224; 544/326; 544/328; 544/329; 546/306; 548/138; 548/143; 548/193; 548/214; 548/233; 548/246; 548/266; 548/315; 548/376; 564/239
[58] Field of Search ................ 544/326, 328, 329, 194, 544/224; 424/251, 249, 250, 263, 269, 276, 272, 273 R, 273 P, 275, 326; 546/306; 548/138, 143, 193, 214, 233, 246, 266, 315, 376; 549/65; 564/239

[56] References Cited

U.S. PATENT DOCUMENTS 4,362,728  12/1982  Yellin ................ 424/249

Primary Examiner—Robert Gerstl
Attorney, Agent, or Firm—Cushman, Darby & Cushman

[57] ABSTRACT

The invention relates to a guanidine derivative of the formula:

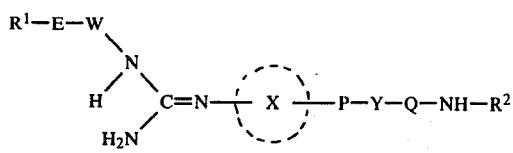

in which W is a 2-6C alkylene chain optionally substituted by 1 or 2 1-4C alkyls; E is O, S, SO, $SO_2$ or $NR^3$ in which $R^3$ is H or 1-6C alkyl; $R^1$ is H or a straight chain 1-6C alkyl optionally substituted by 1 or 2 1-4C alkyls; or $R^1$ and $R^3$ are joined to form a morpholine, pyrrolidine, piperidine or piperazine ring; X, P, Y, Q and $R^2$ are as defined in the specification, and the pharmaceutically-acceptable acid-addition salts thereof. Manufacturing process, pharmaceutical compositions and intermediates are also described. The compounds of the formula I are histamine H-2 antagonists.

8 Claims, No Drawings

SUBSTITUTED GUANIDINE DERIVATIVES, PROCESSES, PHARMACEUTICAL COMPOSITIONS AND METHODS AND INTERMEDIATES

This invention relates to guanidine derivatives which are histamine H-2 antagonists and which inhibit gastric acid secretion.

It is postulated that the physiologically-active compound histamine, which occurs naturally within the human body, is able to combine, in the course of exerting its activity, with certain specific receptors of which there are at least two distinct and separate types. The first has been named the H-1 receptor (Ash and Schild, *Brit. J. Pharmac*, 1966, 27, 427) and the action of histamine at this receptor is blocked (antagonised) by classical "antihistamine" drugs such as mepyramine. The second histamine receptor has been named the H-2 receptor (Black et al., *Nature*, 1972, 238, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In Belgian Pat. No. 866,155, U.S. Pat. Nos. 4,165,377 and 4,165,378 and European Patent Specifications Publication Nos. 0006286, 0006679, 0010418 and 0010894 there are described histamine H-2 receptor antagonists which are guanidine heterocycles carrying a side chain to the end of which is attached a variously-modified guanidine residue. It has now been discovered that if the guanidine radical attached to the heterocyclic ring carries a substituted alkyl radical there are produced compounds which are potent histamine H-2 receptor antagonists.

According to the invention there is provided a guanidine derivative of the formula:

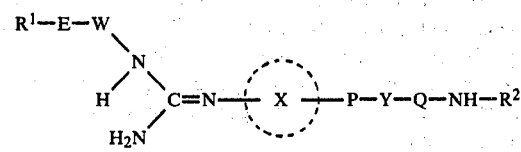

in which
W is a straight chain 2–6C alkylene chain optionally substituted by one or two 1–4C alkyl radicals;
E is an oxygen or sulphur atom, a sulphinyl or sulphonyl radical, or a radical of the formula $NR^3$ in which $R^3$ is a hydrogen atom or a 1–6C alkyl radical;
$R^1$ is hydrogen atom or a straight-chain 1–6C alkyl radical optionally substituted by one or two 1–4C alkyl radicals; or
$R^1$ and $R^3$ are alkyl and are joined to form, together with the nitrogen atom to which they are attached, a morpholine, pyrrolidine, piperidine or piperazine ring;
ring X is a phenyl ring carrying 1 or 2 optional substituents or a 5- or 6-membered heterocyclic aromatic ring containing 1, 2 or 3 hetero atoms selected from oxygen, nitrogen and sulphur atoms, which heterocyclic ring may, where possible, carry a single optional substituent, the optional substituents on ring X being selected from fluorine, chlorine, bromine and iodine atoms and 1–6C alkyl, 1–6C alkoxy, 1–6C alkylthio, trifluoromethyl, hydroxy and amino radicals;
Y is an oxygen or sulphur atom, a direct bond, a methylene, cis or trans vinylene or sulphinyl radical or a radical of the formula $NR^4$ in which $R^4$ is a hydrogen atom of a 1–6C alkyl radical;
P is a direct bond or a 1–4C unbranched alkylene radical optionally substituted by one or two 1–4C alkyl radicals;
Q is a 1–4C unbranched alkylene radical optionally substituted by one of two 1–4C alkyl radicals, provided that when Y is an oxygen atom, a sulphinyl radical or a radical of the formula $NR^4$, Q is a 2–4C optionally substituted alkylene radical;
—$R^2$ is a radical of the formula —A—B in which A is a 3,4-dioxocyclobuten-1,2-diyl radical or a radical of the formula C=Z in which Z is a sulphur or oxygen atom or a radical of the formula NCN, $NNO_2$, $CHNO_2$, $NCONH_2$, $C(CN)_2$, $NCOR^5$, $NCO_2R^5$, $NSO_2R^5$ or $NR^6$ in which $R^5$ is a 1–6C alkyl, 1–6C haloalkyl, 7–10C alkylaryl or 6–10C aryl radical or a 5- or 6-membered heterocyclic aromatic radical containing 1, 2 or 3 hetero atoms selected from oxygen, nitrogen and sulphur atoms and $R^6$ is a hydrogen atom or a 1–6C alkyl, 1–6C haloalkyl, 7–10C alkylaryl or 6–10C aryl radical or —A— is a radical of the formula:

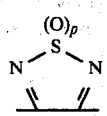

in which p is 1 or 2, and B is a 1–6C alkyl, 1–6C alkoxy or 1–6C alkylthio radical or a radical of the formula $NR^7R^8$ in which $R^7$ and $R^8$, which may be the same or different, are hydrogen atoms or 1–6C alkyl, 1–6C haloalkyl, 2–6C alkoxycarbonyl, 3–6C alkenyl, 3–6C alkynyl (in which the double or triple bond respectively is separated from the nitrogen atom of $NR^7R^8$ by at least one carbon atom), 2–6C (primary hydroxy)alkyl, 2–6C (primary amino)alkyl, 3–8C alkylaminoalkyl, 4–8C dialkylaminoalkyl (in the latter two of which the nitrogen atom is separated from the nitrogen atom of $NR^7R^8$ by at least two carbon atoms), 6–10C aryl or 3–8C cycloalkyl radicals, or $R^7$ and $R^8$ are alkyl and are joined to form, together with the nitrogen atom to which they are attached, a 5- or 6-membered saturated ring which optionally contains an oxygen atom or an $NR^9$ radical in which $R^9$ is a hydrogen atom or a 1–6C alkyl radical;
or —$R^2$ is a radical of the formula:

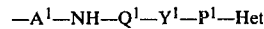

in which $Q^1$, $Y^1$ and $P^1$ have one of the values given above for Q, Y and P respectively, $A^1$ has one of the values given above for A, or —$A^1$— is a radical of the formula:

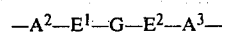

in which $A^2$ and $A^3$, which may be the same or different, have one of the values given above for A, $E^1$ and $E^2$, which may be the same or different, are oxygen or sulphur atoms or NH radicals, G is a 2–12C alkylene, 2–12C alkenylene, 2–12C alkynylene or 2–12C hydroxyalkylene radical and Het— is a radical of the formula:

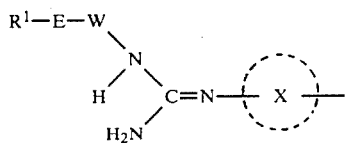

in which $R^1$, E, W and ring X have the meanings stated above, or Het— is a radical of the formula:

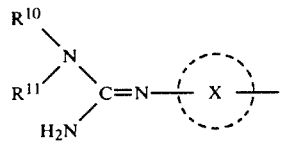

in which ring X has the meaning stated above and $R^{10}$ and $R^{11}$, which may be the same or different, are hydrogen atoms or 1–10C branched or unbranched alkyl, 3–8C cycloalkyl or cycloalkylalkyl radicals in which the cycloalkyl part is 3–8C and the alkyl part is 1–6C, each alkyl, cycloalkyl and cycloalkylalkyl radical being optionally substituted by one or more halogen atoms selected from fluorine, chlorine and bromine atoms, provided that at least one of $R^{10}$ and $R^{11}$ is a halogen-substituted alkyl, cycloalkyl or cycloalkylalkyl radical and provided there is no halogen substituent on the carbon atom of the alkyl, cycloalkyl or cycloalkylalkyl radical which is directly attached to the nitrogen atom;

or Het— is an oxazol-4-yl, thiazol-4-yl or imidazol-4-yl radical substituted in the 2-position by a radical of the formula:

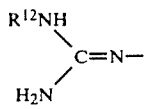

or Het— is a 1,2,4-thiadiazol-3-yl or 1,2,4-oxadiazol-3-yl radical substituted in the 5-position by a radical of the formula VII, in which $R^{12}$ is a hydrogen atom or a 1–6C alkyl, 1–6C alkanoyl or 7–11C aroyl radical;

or Het is an unfused nitrogen-containing 5- or 6-membered monocyclic heterocyclic ring which is optionally substituted by a 1–6C alkyl, 1–6C alkoxy, hydroxy, trifluoromethyl, hydroxymethyl or amino radical or by a halogen atom;

or Het— is a radical of the formula:

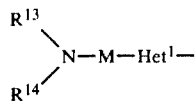

in which $R^{13}$ and $R^{14}$, which may be the same or different, are hydrogen atoms or 1–8C alkyl, 3–8C alkenyl, 3–8C alkynyl, 3–8C cycloalkyl, 1–8C trifluoroalkyl or 1–6C alkyl substituted by a hydroxy, 1–6C alkoxy, amino, 1–6C alkylamino, 3–8C cycloalkyl, 2–8C dialkylamino radical or 6–10C aryl radical or $R^{13}$ and $R^{14}$ are alkyl and are joined to form, together with the nitrogen atom to which they are attached, a 5- or 10-membered alicyclic heterocyclic ring; M is a 1–6C straight or branched chain alkylene radical and —Het$^1$— is a furan or thiophene ring linked through the 2 and 5 positions, a pyridine ring linked through the 2 and 6 positions or a phenyl ring linked through the 1 and 3 or 1 and 4 positions;

or —$R^2$ is a radical of the formula:

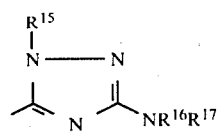

in which $R^{15}$ is a hydrogen atom or a 1–6C alkyl, 3–6C alkenyl, 1–6C hydroxyalkyl or 2–6C alkoxyalkyl radical, a 6–10C aryl radical or an arylalkyl radical in which the aryl part is 6–10C and the alkyl part is 1–6C and $R^{16}$ and $R^{17}$, which may be the same or different are hydrogen atoms, 1–6C alkyl, 3–6C alkenyl, 2–6C hydroxyalkyl, 3–6C alkoxyalkyl or phenylalkyl or pyridylalkyl radicals in which the alkyl part is 1–6C, or $R^{16}$ and $R^{17}$ are alkyl and are joined to form, together with the nitrogen atom to which they are attached, a 5- or 7-membered saturated heterocyclic ring which may optionally contain an oxygen atom or an NH radical, or $R^{16}$ and $R^{17}$ taken together represent the group $=CR^{18}R^{19}$ in which $R^{18}$ is a phenyl or pyridyl radical and $R^{19}$ is a hydrogen atom or a 1–6C alkyl radical;

or —$R^2$ is a radical of the formula:

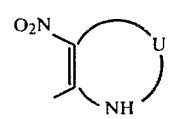

in which U is a 2–4C alkylene radical which is optionally substituted by one or two radicals selected from 1–6C alkyl, phenylalkyl, furylalkyl, thienylalkyl and pyridylalkyl radicals in which the alkyl part is 1–6C and the phenyl or heterocyclic ring is optionally substituted by 1 or 2 halogen atoms or methyl or methoxy radicals;

or —U— is a radical of the formula:

$$-CH_2-NR^{20}-CH_2-\quad\quad XI$$

in which $R^{20}$ is one of the optional substituents, given above, on U when it is an alkylene radical;

or —$R^2$ is a radical of the formula:

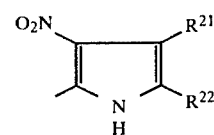

in which $R^{21}$ is a hydrogen atom or one of the optional substituents on U, given above, when it is an alkylene radical and $R^{22}$ is a hydrogen atom or a 1–6C alkyl radical;

or —$R^2$ is a radical of the formula XIII, XIV, XV or XVI:

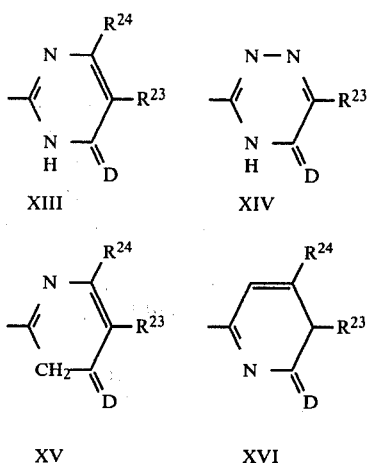

in which D is an oxygen or sulphur atom, $R^{24}$ is a hydrogen atom or 1-6C alkyl radical and $R^{23}$ is a hydrogen atom, 1-6C alkyl radical or a radical of the formula:

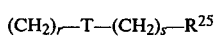            XVII in which

T is an oxygen or sulphur atom or a methylene radical;

r and s together are 1 to 4 when T is an oxygen or sulphur atom and r and s together are 0 to 4 when T is a methylene radical;

$R^{25}$ is a 3-6C cycloalkyl radical or a naphthyl radical or a phenyl radical optionally substituted by a methylenedioxy or ethylenedioxy radical or, in the 2, 3, 4 or 5 positions, by one or more (same or different) halogen atoms or 1-6C alkyl, 1-6C alkoxy or 1-6C haloalkyl radicals, arylalkoxy radicals in which the aryl part is 6-10C and the alkoxy part is 1-6C, 3-8C alkoxyalkoxy radicals, 2-8C dialkylamino radicals, alkoxyphenyl or alkoxyphenoxy radicals in which the alkoxy part is 1-6C, hydroxy, phenyl, halophenyl or phenoxy radicals or $R^{25}$ is a pyridine, pyridine-N-oxide, furan, thiophene, thiazole, pyridazine, thiadiazole, quinoline, isoquinoline, benzimidazole, benzthiazole or indole heterocyclic ring each optionally substituted by a halogen atom, a 1-6C alkyl or 1-6C alkoxy radical or a hydroxy or amino radical;

or —$R^2$ is a pyrimid-2-yl or imidazol-2-yl radical to which is optionally fused a benzene ring, the pyrimidine and imidazole rings, or alternatively the optionally fused benzene ring, carrying 1 or 2 optional substituents selected from the group which is optionally substituted on ring X;

and the pharmaceutically-acceptable acid-addition salts thereof.

It is to be understood that, in the above formulae I, V, VI, VII, IX, X, XII, XIII, XIV, XV and XVI and throughout this specification, although the double bonds in both side chains attached to ring X have been inserted in particular positions, various other tautomeric forms are possible, and this invention includes such tautomeric forms within its scope, both in terms of the compound of the invention and in terms of the manufacturing processes. It is further to be understood that the letters C, H, N O and S are the universally accepted contractions for the elements carbon, hydrogen, nitrogen, oxygen and sulphur respectively. Unless otherwise specified, "halogen" includes fluorine, chlorine, bromine and iodine.

A particular value for the optional substituent on W is a methyl radical.

A particular value for $R^1$ or $R^3$ is a hydrogen atom or a methyl radical.

A particular value for the optional substituent on $R^1$ is a methyl radical.

A particular value for ring X is a phenyl, thiophene, pyridine, pyrimidine, imidazole, thiazole, oxazole, pyrazole, triazole, thiadiazole, oxadiazole, pyrazine, pyridazine, isothiazole, isoxazole or triazine ring.

A particular value for the optional substituent on ring X when it is an alkyl, alkoxy or alkylthio radical is a methyl, methoxy or methylthio radical.

A particular value for $R^4$ when it is an alkyl radical is a methyl radical.

A particular value for the optional substituent on P or Q is a methyl radical.

A particular value for $R^5$ is a methyl, ethyl, n-propyl, i-propyl, n-butyl, trifluoromethyl, 2,2,2-trifluoroethyl, phenyl, p-tolyl or pyridyl radical.

A particular value for $R^6$ is a hydrogen atom or a methyl, 2,2,2-trifluoroethyl, phenyl or p-tolyl radical.

A particular value for B when it is an alkyl, alkoxy or alkylthio radical is a methyl, ethyl, methoxy, ethoxy or methylthio radical.

A particular value for $R^7$ or $R^8$ is a hydrogen atom or a methyl, ethyl, i-propyl, 2,2,2-trifluoroethyl, methoxycarbonyl, ethoxycarbonyl, allyl, propargyl, 2-hydroxyethyl, 2-aminoethyl, 2-methylaminoethyl, 2-dimethylaminoethyl, 2-diethylaminoethyl, cyclohexyl or phenyl radical.

A particular value for $R^7$ and $R^8$ when they are joined to form a ring is a pyrrolidine, piperidine, morpholine or piperazine ring.

A particular value for $R^9$ is a hydrogen atom or a methyl radical.

A particular value for G is an ethylene, trimethylene, tetramethylene, but-2-enylene, but-2-ynylene or 2-hydroxytrimethylene radical.

A particular value for $R^{10}$ or $R^{11}$ when it is a substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4,4-heptafluorobutyl radical.

A particular value for $R^{10}$ or $R^{11}$ when it is a substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^{10}$ or $R^{11}$ when it is a substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for $R^{10}$ or $R^{11}$ when it is an alkyl radical is a methyl, ethyl, propyl, isopropyl or butyl radical.

A particular value for $R^{10}$ or $R^{11}$ when it is a cycloalkyl radical is a cyclopropyl or cyclobutyl radical.

A particular value for $R^{10}$ or $R^{11}$ when it is a cycloalkylalkyl radical is a cyclopropylmethyl or cyclobutylmethyl radical.

A particular value for $R^{13}$ or $R^{14}$ is a hydrogen atom or a methyl, allyl, propargyl, cyclohexyl, trifluoromethyl, 2-hydroxyethyl, 2-methoxyethyl, 2-aminoethyl, 2-methylaminoethyl, 2-dimethylaminoethyl, cyclopropylmethyl or benzyl radical.

A particular value for $R^{12}$ is a hydrogen atom or a methyl, n-butyl, acetyl, propionyl or benzoyl radical.

A particular value for the optional substituent on Het when it is an alkoxy or alkylthio radical is a methoxy or methylthio radical.

A particular value for $R^{13}$ and $R^{14}$ when they are joined to form a ring is a pyrrolidine, piperidine, piperazine or morpholine ring.

A particular value for M is a methylene, ethylene or trimethylene radical.

A particular value for $R^{15}$ is a hydrogen atom or a methyl, allyl, 2-hydroxyethyl, 2-methoxyethyl, phenyl or benzyl radical.

A particular value for $R^{16}$ or $R^{17}$ is a hydrogen atom or a methyl, allyl, 2-hydroxyethyl, 2-methoxyethyl, benzyl or pyridylmethyl radical.

A particular value for $R^{16}$ and $R^{17}$ when they are joined to form a ring is a pyrrolidine, piperidine, piperazine or morpholine ring.

A particular value for $R^{19}$ when it is an alkyl radical is a methyl radical.

A particular value for the optional substituent on U when U is an alkylene radical is a methyl, benzyl, 2-furylmethyl, 2-thienylmethyl or 2-pyridylmethyl radical.

A particular value for $R^{20}$ is one of the particular values given above for the optional substituent on U when it is an alkylene radical.

A particular value for $R^{21}$ is a hydrogen atom or one of the particular values given above for the optional substituent on U when U is an alkylene radical.

A particular value for $R^{22}$ is a hydrogen atom or a methyl radical.

A particular value for $R^{23}$ or $R^{24}$ when it is an alkyl radical is a methyl radical.

A particular value for $R^{25}$ when it is a cycloalkyl radical is a cyclohexyl radical.

A particular value for the optional substituent on $R^{25}$ when $R^{25}$ is a phenyl radical is a fluorine, chlorine or bromine atom or a methylenedioxy, ethylenedioxy, methyl, methoxy, trifluoromethyl, benzyloxy, 2-methoxyethoxy, dimethylamino, 4-methoxyphenyl, 4-methoxyphenoxy, hydroxy, phenyl, 4-chlorophenyl, 4-bromophenyl or phenoxy radical.

A particular value for the optional substituent on $R^{25}$ when $R^{25}$ is a heterocyclic ring is a fluorine, chlorine or bromine atom or a methyl, methoxy, hydroxy or amino radical.

A particular value for the optional substituent on $R^2$ when $R^2$ is a pyrimid-2-yl or imidazol-2-yl radical to which is optionally fused a benzene ring is one of the particular values for the optional substituent on ring X given above.

The following are ten preferred features of the guanidine derivative of the formula I. When any one of these features is taken, either singly or in combination, with the other general or particular features of the guanidine derivative of the formula I listed above, there are obtained preferred sub-groups of compounds within the above general definition.

1. $R^1$ is an optionally-substituted alkyl radical and E is an oxygen or sulphur atom.
2. Ring X is a pyridine, pyrimidine, triazole, pyrazole or thiadiazole ring.
3. —$R^2$ is a radical of the formula —A—B in which A is a radical of the formula C=Z in which Z is a radical of the formula $NCN$, $CHNO_2$ or $NSO_2R^5$ and B is a radical of the formula $NHR^7$.
4. —$R^2$ is a radical of the formula —A—B in which A is a radical of the formula II and B is a radical of the formula $NHR^7$.
5. —$R^2$ is a radical of the formula XII.
6. —$R^2$ is a radical of the formula IX.
7. $R^1$ is a methyl radical, E is an oxygen or sulphur atom and W is an ethylene or propylene chain.
8. Ring X is a pyrimidine ring in which the guanidine radical is substituted at the 2-position and P is substituted at the 4-position, a 2,6-disubstituted pyridine ring, a 1,3-disubstituted triazole ring or a pyrazole ring in which the guanidine is substituted at the 3-position and P is substituted at the 1-position.
9. Y is a direct bond and P+Q is a tetramethylene or pentamethylene chain.
10. Y is a sulphur or oxygen atom, P is a direct bond and Q is an ethylene, propylene or tetramethylene radical.

Specific compounds of the invention are set out in the Examples. The following is a preferred group of compounds:

2-[2-(2-methoxyethyl)guanidino]-4-[4-(2-cyano-3-methylguanidino)butyl]thiazole (Example 1);

2-[2-(2-methoxyethyl)guanidino]-4-[4-(2-methylsulphonyl-3-methylguanidino)butyl]thiazole (Example 2);

2-[2-(2-methylthioethyl)guanidino]-4-[4-(2-cyano-3-methylguanidino)butyl]thiazole (Example 6);

1-[5-(2-[2-methoxyethyl]guanidinothiazol-4-yl)pentylamino]-1-methylamino-2-nitroethylene (Example 9);

2-[2-(2-methoxyethyl)guanidino]-4-[5-(2-cyano-3-methylguanidino)pentyl]thiazole (Example 10);

2-[4-(2-cyano-3-methylguanidino)butyl]-4-[2-(2-methoxyethyl)guanidino]pyrimidine (Example 13);

and the pharmaceutically-acceptable acid-addition salts thereof.

Of these a particularly preferred compound is that of Example 13.

A suitable pharmaceutically-acceptable acid-addition salt of the guanidine derivative of the invention is, for example, a salt formed with hydrochloric, hydrobromic, phosphoric, sulphuric, acetic, citric or maleic acid.

The guanidine derivative of the invention may be manufactured by methods known in themselves for the manufacture of chemically-analogous compounds. The following processes, (X, Y, A, B, $A^1$, $A^2$, $A^3$, $E^1$, $E^3$, G, W, p, r, s, Het, $Het^1$, U, D and $R^1$ to $R^{23}$ inclusive having the meanings stated above), are therefore provided as further features of the invention.

The process of the invention is characterised by:

(a) reaction of a compound of the formula:

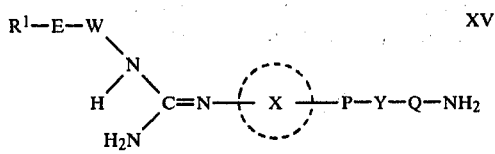
XVIII with a compound of the formula $R^{26}$—$R^2$ in which $R^{26}$ is a displaceable radical. When $R^2$ is a radical of the formula A—B or of the formula III, $R^{26}$ is preferably a methoxy, ethoxy or methylthio radical. When $R^2$ is a radical of the formula IX, X, XII, XIII, XIV, XV or XVI or a pyrimid-2-yl or imidazol-2-yl radical, $R^{26}$ is preferably a halogen atom, a methylthio or benzylthio radical. The reaction may be carried out in the absence of a diluent or solvent, or in the presence of a diluent or solvent such as methanol, ethanol, acetonitrile or pyridine. The reaction may be accelerated or completed by the application of heat, for example by heating to the boiling point of the diluent or solvent.

(b) for those compounds in which —$R^2$ is a radical of the formula —A—B in which B is an alkoxy or alkylthio radical or a radical of the formula $NR^7R^8$ or —$R^2$ is a radical of the formula III, reaction of a compound of the formula:

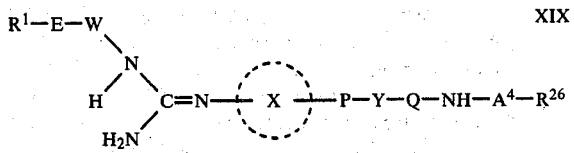
XIX in which $R^{26}$ is a displaceable radical and $A^4$ has one of the values given for A or $A^1$ with a compound of the formula $R^{27}$—H in which $R^{27}$ is a 1-6C alkoxy or 1-6C alkylthio radical, a radical of the formula $NR^7R^8$ or a radical of the formula:

NH—$Q^1$—$Y^1$—$P^1$—Het    XX

The process may be carried out using an excess of $R^{27}$—H. $R^{26}$ is preferably a methoxy, ethoxy or methylthio radical. The process may be carried out in a diluent or solvent such as water, methanol, ethanol or pyridine. The process may be accelerated by the application of heat, for example by heating to the boiling point of the diluent or solvent.

(c) for those compounds in which —$R^2$ is a radical of the formula —A—B in which A is a radical of the formula C=Z in which Z is a sulphur or oxygen atom and B is a radical of the formula $NR^7R^8$ in which $R^8$ is a hydrogen atom and $R^7$ has the value stated above other than a hydroxyalkyl, aminoalkyl, or alkylaminoalkyl radical, or —$R^2$ is a radical of the formula III in which $A^1$ is a radical of the formula C=Z in which Z is a sulphur or oxygen atom, reaction of a compound of the formula XVIII with a compound of the formula $R^{28}$—N=C=D, or alternatively reaction of a compound of the formula:

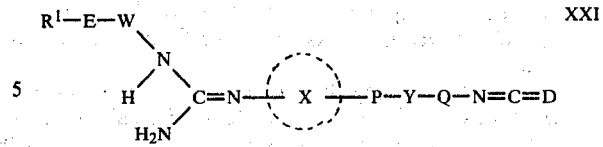
XXI with a compound of the formula $R^{28}$—$NH_2$ in which D is a sulphur or oxygen atom and $R^{28}$ is a hydrogen atom or an alkyl, haloalkyl, alkenyl, alkynyl, dialkylaminoalkyl, cycloalkyl or phenyl radical, or a radical of the formula:

—$Q^1$—$Y^1$—$P^1$—Het    XXII

When D is a sulphur atom the reaction is preferably carried out in a diluent or solvent such as methanol or ethanol. When D is an oxygen atom a non-alcoholic diluent or solvent must be used.

(d) reaction of a compound of the formula:

XXIII with ammonia. The process may be carried out in ethanol or methanol which is saturated with ammonia.

(e) for those compounds in which —$R^2$ is a radical of the formula —A—B in which A is a radical of the formula C=Z in which Z is a radical of the formula NCN and B is a radical of the formula $NR^7R^8$ in which $R^7$ and $R^8$ are hydrogen atoms, reaction of a compound of the formula XVIII with dicyanimide or a salt thereof. The process is preferably carried out using the sodium salt of dicyanimide, in a diluent or solvent such as n-butanol. The reaction may be accelerated or completed by the application of heat, for example by heating to the boiling point of the diluent or solvent.

(f) for those compounds in which —$R^2$ is a radical of the formula IX in which $R^{15}$ is other than a hydroxyalkyl radical and $R^{16}$ and $R^{17}$ are hydrogen atoms, reaction of a compound of the formula I in which —$R^2$ is a radical of the formula —A—B in which A is a radical of the formula C=Z in which Z is a radical of the formula NCN and B is an alkoxy or alkylthio radical, with a compound of the formula:

$H_2NNHR^{29}$    XXIV in which $R^{29}$ is a hydrogen atom or an alkyl, alkenyl, alkoxyalkyl, aryl or arylalkyl radical. The process may be carried out in a diluent or solvent such as ethanol or dimethylformamide, and may be accelerated or completed by heating, for example by heating to the boiling point of the diluent or solvent.

(g) for those compounds in which —$R^2$ is a radical of the formula A—B in which B is a radical of the formula C=Z, reaction of a compound of the formula XVIII with a compound of the formula:

Z=C=$NR^7$    XXV

The process may be carried out in a diluent or solvent such as ethanol or dimethylformamide.

(h) for those compounds in which the optional halogen substituent on ring X is a chlorine or bromine atom, chlorination or bromination of the corresponding unsubstituted compound. The reaction may be carried out in a diluent or solvent such as chloroform or methylene chloride.

(i) for those compounds in which —$R^2$ is a radical of the formula —A—B in which A is a radical of the formula C=Z in which Z is a radical of the formula $NR^6$ and B is a radical of the formula $NHR^7$, reaction of a compound of the formula:

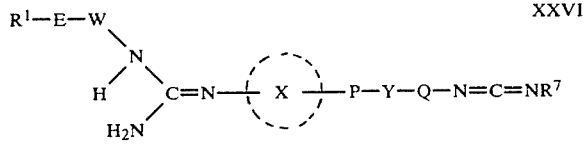
XXVI with a compound of the formula $R^6NH_2$. The reaction may be carried out in a diluent or solvent such as dimethylformamide.

(j) for those compounds in which —$R^2$ is a radical of the formula —A—B in which A is a radical of the formula C=Z in which Z is an oxygen or sulphur atom and B is an alkyl radical, reaction of a compound of the formula XVIII with an acid, or an acylating agent derived from an acid, of the formula $R^{30}CD_2H$ in which $R^{30}$ is a hydrogen atom or a 1-6C alkyl radical and D is an oxygen or sulphur atom. The process may be carried out in an inert diluent or solvent, and in the presence of a base, at or below room temperature. The diluent or solvent preferably is, or contains, pyridine which also acts as the base. When D is an oxygen atom, the reaction is preferably carried out using the acid chloride or acid anhydride as the acylating agent.

(k) for those compounds in which $R^2$ is an imidazol-2-yl radical to which is fused an optionally-substituted benzene ring, cyclisation of a compound of the formula:

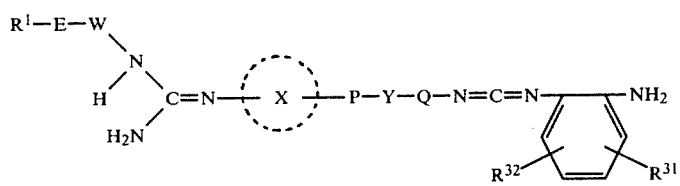
XXVII in which $R^{31}$ and $R^{32}$ are the optional substituents on the benzene ring. The process may be conducted in a diluent or solvent such as dimethylformamide.

(l) for those compounds in which Y is a sulphinyl radical, oxidation of the corresponding compound in which Y is a sulphur atom. The process may be carried out using a mild oxidising agent such as sodium metaperiodate, in a diluent or solvent such as aqueous methanol or aqueous ethanol.

(m) for those compounds in which —$R^2$ is a radical of the formula —A—B or III in which A, $A^1$, $A^2$ or $A^3$ is a radical of the formula C=Z in which Z is a radical of the formula $NCONH_2$, hydrolysis of the corresponding compound in which Z is a radical of the formula NCN. The process may be carried out using a dilute mineral acid, for example dilute hydrochloric acid, in a diluent or solvent such as water. The reaction may be accelerated or completed by the application of heat, for example by heating to the boiling point of the diluent or solvent.

(n) for those compounds in which Y is an oxygen or sulphur atom or a radical of the formula $NR^4$, reaction of a compound of the formula:

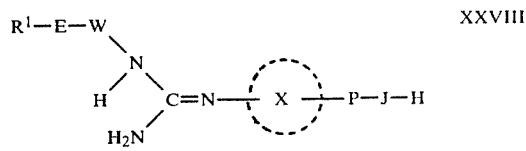
XXVIII in which J is an oxygen or sulphur atom or a radical of the formula $NR^4$ with a compound of the formula:

$$R^{26}-Q-NH-R^2 \qquad XXIX$$

in which $R^{26}$ is a displaceable radical.

When the process of the invention manufactures the compound of the formula I in the form of the free base and an acid-addition salt is required, the compound of the formula I in the free base form is reacted with an acid which affords a pharmaceutically-acceptable anion.

A critical starting material for use in a number of the above processes is the compound of the formula XVIII. This compound may also be used as an intermediate in the preparation of starting materials for a number of other processes. The compound of the formula XVIII is therefore considered to be a further feature of the invention.

The compound of the formula XVIII may be prepared in a number of ways depending on the nature of the ring X and on the nature of Y. In general terms the two side chains attached to ring X may be constructed one before the other, in either order, starting either from a suitably substituted ring X or by constructing ring X itself from subfragments. When Y is a direct bond, a methylene or vinylene radical, it is generally convenient to start with a ring X carrying this side chain in which the terminal nitrogen atom is suitably protected (for example in the form of a phthalimido residue) or so to construct ring X that such a side chain is inserted at the same time. On the other hand when Y is an oxygen or sulphur atom, a sulphinyl radical or a radical of the formula $NR^4$, it is generally convenient to introduce Y at a later stage of the synthesis. These general principles can be illustrated with reference to syntheses of specific ring systems.

When ring X is a pyrimidine in which the guanidine is attached to the 4-position and the other side chain to the 2-position and Y is a direct bond, a methylene or vinylene radical, the compound of the formula XVIII may be obtained as follows. Reaction of a compound of the formula:

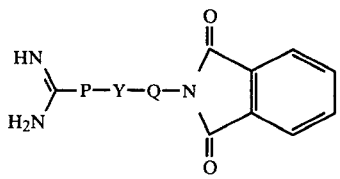

XXX with an optionally substituted 3-chloroacrylonitrile gives the 2-substituted-4-aminopyrimidine. This compound is then reacted with a compound of the formula:

$$R^1-E-W-NCS$$

to form the corresponding thiourea which is treated with ammonia in the presence of mercuric oxide to give the guanidine (via the carbodiimide as intermediate). Finally the amine is liberated from its protecting group.

When ring X is a pyrimidine in which the guanidine is attached to the 4-position and the other side chain to the 2-position and Y is a sulphur or oxygen atom or a radical of the formula $NR^4$, the compound of the formula XVIII may be obtained as follows. A compound of the formula:

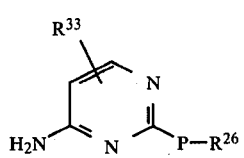

XXI in which $R^{26}$ is a displaceable radical and $R^{33}$ is the optional substituent on ring X is reacted with a compound of the formula:

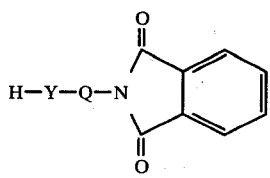

XXXII to give the compound of the formula:

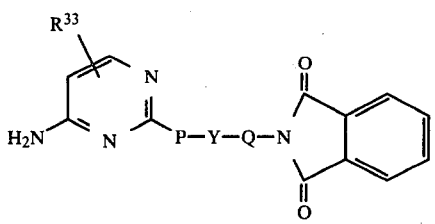

XXXIII

The free amino radical is then elaborated to form the substituted guanidine, as described above, and the amine is finally liberated from the protecting group. In an alternative sequence the positions of $R^{26}$ and Y—H are interchanged.

When ring X is a thiazole ring in which the guanidine is attached to the 2-position and the other side chain to the 4-position and Y is a sulphur or oxygen atom or a radical of the formula $NR^4$, the compound of the formula XVIII may be obtained as follows. An amine of the formula $R^1$—E—W—$NH_2$ is reacted with sodium dicyanimide to give the compound of the formula:

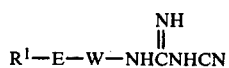

XXXIV which is in turn reacted with thioacetamide and an acid (a source of $H_2S$) to give the amidinothiourea of the formula:

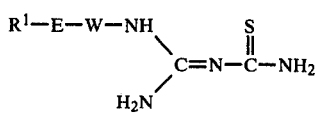

XXXV

This amidinothiourea is then reacted with a compound of the formula:

$$ClCHR^{34}CO-P-Cl$$

XXXVI in which $R^{34}$ is a hydrogen atom or the optional substituent on ring X to give the compound of the formula:

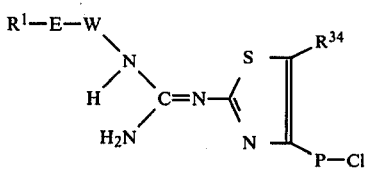

XXXVII

This compound is then reacted with a compound of the formula:

$$H-Y-Q-NH_2$$

XXXVIII to give the compound of the formula XVIII. This reaction sequence is illustrated in Example 7.

When ring X is a thiazole ring in which the guanidine is attached to the 2-position and the other side chain to the 4-position and Y is a direct bond, a methylene or vinylene radical, the compound of the formula XVIII may be obtained as follows. The compound of the formula XXXV is reacted with a compound of the formula:

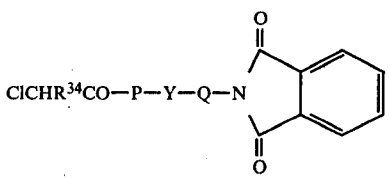

XXXIX in which $R^{34}$ is a hydrogen atom or the optional ring substituent to give the compound of the formula:

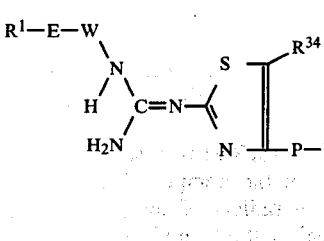

XL

The protecting group is then removed to give the required product. This reaction sequence is illustrated in Examples 1, 4, 5, 8 and 10.

The above general methods can be applied to other substitution patterns within the same ring X systems, and can also be applied to other ring X systems not discussed above. Alternatively, Smith, Kline and French patents describe a number of different compounds of the general formula:

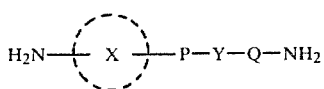   XLI

In this type of compound, the amino group attached to Q is much more basic than that attached to ring X, and the former may thus be selectively reacted with a protecting group. The guanidine residue may then be formed by one of the methods described above and finally the protecting group removed to give the compound of the formula XVIII.

When Y is a sulphinyl radical, the compound of the formula XVIII may be prepared by mild oxidation of the corresponding compound in which Y is a sulphur atom.

The compound of the formula XIX for use in process (b) may be prepared by reaction of the compound of the formula XVIII with a compound of the formula $R^{26}—A^4—R^{26}$, for example as described in Examples 1, 2, 4, 5, 7 and 10.

The compound of the formula XXI for use in process (c) may be prepared by reaction of the compound of the formula XVIII with thiocarbonyldimidazole or carbonyldiimidazole.

The compound of the formula XXIII for use in process (d) may be prepared by reaction of a compound of the formula:

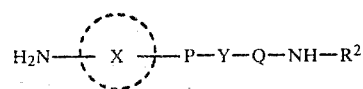   XLII (many of which are known compounds, others of which may be prepared by modifications of the processes described above) with a compound of the formula $R^1$—E—W—NCS to give the corresponding thiourea. This thiourea is treated with yellow mercuric oxide to give the carbodiimide of the formula XXIII which is preferably then reacted as described in process (d) in situ without isolation.

The compound of the formula XXV for use in process (g) may be prepared by reaction of a compound of the formula:

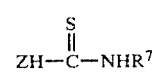   XLIII with yellow mercuric oxide or silver nitrite to give the carbodiimide which is preferably reacted as described in process (g) in situ without isolation.

The compound of the formula XXVI for use in process (i) may be prepared from the compound of the formula I in which $—R^2$ is a radical of the formula A—B in which A is a radical of the formula C=Z in which Z is a sulphur atom and B is a radical of the formula $NR^7R^8$ in which $R^8$ is a hydrogen atom by reaction with yellow mercuric oxide to give the carbodiimide which is preferably reacted as described in process (i) in situ without isolation.

The compound of the formula XXVII for use in process (k) may be prepared by reaction of a compound of the formula XXI in which D is a sulphur atom with a compound of the formula:

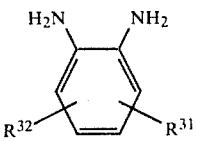   XLIV

The resulting thiourea is treated with silver nitrate and the carbodiimide of the formula XXVII thus formed is preferably reacted as described in process (k) in situ without isolation.

As noted below, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$, 5% $CO_2$) Krebs-Hanseleit buffer (pH 7.4). The tissue is allowed to stabilise over 1 hour during which time it is washed 2-4 times. Individual contractions are recorded with a force-displacement transducer through a strain gauge coupler, and instantaneous rates are monitored with a cardiotachometer. A control response to 1 $\mu M$ histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu M$) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 $\mu M$., and the more active compounds show complete inhibition of response at this concentration.

The histamine-stimulated cyclic AMP test is carried out as described by Scholes et al, *Agents and Actions*, 1976, 6, 677–682.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continous intravenous infusion of secretagogue (0.5 μmole/kg/hour of histamine or 2 μg/kg./hour pentagastrin) in saline (15 ml./hour) is begun. Gastric acid samples are collected every 15 minutes. The volume of each sample is measured and 1 ml. aliquot is titrated to neutrality with 0.1 NNaOH to determine acid concentration. When a plateau of secretion is reached (1-2 hours), the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes is ascertained and the test compound, contained in 25 Ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test are predictive of activity in the dog test.

No overt toxicity or side effects were noted during the dog tests.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or pareneteral administration may also contain, or be co-administered with, one or more known drugs selected from antacids, for example aluminium hydroxide—magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or asprin; prostaglandsin, for example 16,16-dimethylprostaglandin $E_2$; classical antihistamines (histamine H-1 antagonists), for example mepyramine or diphenyldramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenyldramine and/or one or more steroidal anti-inflammatory agents, for example fluocinolone or triamcinolone.

A topical formulation may contain 1-10% w/w of the guanidine derivative of the invention. A preferred pharmaceutical composition of the invention is one suitable for oral administration in unit dosage form, for example a tablet or capsule which contains between 10 mg. and 500 mg. of the guanidine derivative, or one suitable for intravenous, subcutaneous or intramulscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each patient will receive an oral dose of between 15 mg. and 1500 mg. and preferably between 20 mg. and 200 mg. of guanidine derivative or an intravenous, subcutaneous or intramuscular dose of between 1.5 mg. and 150 mg., and preferably between 5 mg. and 20 mg. of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1-4 times per day.

The invention is illustrated, but not limited, by the following Examples in which the temperatures are in degrees Centigrade. The n.m.r. spectra are quoted in δ relative to tetramethylsilane (δ=0) as an internal standard (s=singlet; d=doublet; t=triplet; m=multiplet; br=broad).

EXAMPLE 1

A mixture of 2-[2-(2-methoxyethyl)guanidino]-4-(4-aminobutyl)thiazole (0.7 g.) and dimethyl (cyanoimido)dithiocarbonate (0.38 g.) in ethanol (14 ml.) was heated under reflux for 5 minutes and then allowed to cool to ambient temperature over 30 minutes. The solution was then evaporated to dryness and the residue, 2-[2-(2-methoxyethyl)guanidino]-4-[4-(3-cyano-2-methylisothioureido)butyl]thiazole, was dissolved in 33% w/v ethanolic methylamine (15 ml.). After two hours the solution was evaporated to dryness and the residue treated in acetone with maleic acid to give 0.7 g. of 2-[2-(2-methoxyethyl)guanidino]-4-[4-(2-cyano-3-methylguanidino)butyl]-thiazole hydrogen maleate, m.p. 155° (decomp.) (Yield 63%).

The 2-[2-(2-methoxyethyl)guanidino]-4-(4-aminobutyl)thiazole used as starting material may be prepared as follows:

A solution of (2-methoxyethyl)amidinothiourea (1.45 g.) and N-(6-chloro-5-oxohexyl)phthalimide (2.0 g.) in ethanol (25 ml.) was heated under reflux for 30 minutes and then evaporated to dryness. The residue was dissolved in ethyl acetate, from which solution crystals appeared on scratching. The solid product was filtered off and air dried to give 2.5 g. of 2-[2-(2-methoxyethyl)-guanidino]-4-(4-phthalimidobutyl)thiazole hydrochloride, m.p. 160°-163°.

This material was heated under reflux in a mixture of ethanol (35 ml.) and water (35 ml.) containing sufficient aqueous sodium hydroxide to give a pH of 11. After 15 minutes the pH was adjusted to 3 with concentrated hydrochloric acid and maintained at this pH by occasional additions of HCl. After a further 15 minutes the pH was again adjusted to 11 with aqueous sodium hydroxide. The solution was then evaporated to dryness and the residue triturated with ethyl acetate (100 ml.). The ethyl acetate was then filtered and evaporated to dryness to give 1.4 g. of 2-[2-(2-methoxyethyl)-guanidino]-4-(4-aminobutyl)thiazole. A sample converted to the di(hydrogen maleate) had m.p. 140°-143°.

EXAMPLE 2

A mixture of 2-[2-(2-methoxyethyl)guanidino]-4-(4-aminobutyl)thiazole (0.54 g.) and dimethyl (methylsulphonylimido)dithiocarbonate (0.4 g.) in ethanol (10 ml.) was allowed to stand at room temperature overnight. It was then evaporated to dryness and the residue, 2-[2-(2-methoxyethyl)guanidino]-4-[4-(3-methylsulphonyl-2-methylisothioureido)butyl]thiazole, was dissolved in 33% w/v ethanolic methylamine (10 ml.). After 4 hours the solution was evaporated to dryness and the residue purified by chromatography on silica gel using chloroform/methanol/concentrated aqueous ammonia (s.g. 0.880) 0:1:0.1 v/v/v. The appropriate fractions were combined and evaporated to dryness and the residue converted to a hydrogen maleate salt in acetone to give 0.42 g. of 2-[2-(2-methoxyethyl)guanidino]-4-[4-(2-methylsulphonyl-3-methylguanidino)butyl]thiazole hydrogen maleate, m.p. 138°-140° (yield 41%).

EXAMPLE 3

A mixture of 2-[2-(2-methoxyethyl)guanidino]-4-(4-aminobutyl)thiazole (0.27 g.) and acetic anhydride (0.12 g.) was heated under reflux in acetonitrile (5 ml.) for 5 minutes, allowed to stand for 1 hour, evaporated to dryness and the residue purified by chromatography on silica gel using chloroform/methanol/concentrated aqueous ammonia (s.g. 0.880) 9:1:0.1 v/v/v as eluant. The appropriate fractions were combined and evaporated to dryness and the residue converted to the hydrogen maleate salt in acetone to give 0.13 g. of 2-[2-(2-methoxyethyl)guanidino]-4-(4-acetylaminobutyl)-thiazole hydrogen maleate, m.p. 161°-163° (yield 31%).

EXAMPLE 4

A mixture of 2-[2-(2-hydroxyethyl)guanidino]-4-(4-aminobutyl)thiazole (0.52 g.) and dimethyl (methylsulphonylimido)dithiocarbonate (0.4 g.) in ethanol (5 ml.) was allowed to stand at room temperature for 16 hours. The solution was then evaporated to dryness and the residue, 2-[2-(2-hydroxyethyl)guanidino]-4-[4-(3-methylsulphonyl-2-methylisothioureido)butyl]thiazole, was dissolved in 33% w/v ethanolic methylamine (20 ml.). After 4 hours the solution was evaporated to dryness and the residue treated with fumaric acid in ethanol to give 0.62 g. of 2-[2-(2-hydroxyethyl)guanidino]-4-[4-(2-methylsulphonyl-3-methylguanidino)butyl]thiazole 0.75 fumarate, m.p. 128°-132° (Yield 64%).

The 2-[2-(2-hydroxyethyl)guanidino]-4-(4-aminobutyl)thiazole used as starting material may be prepared as follows:

To ethanolamine (30 ml.) in water (200 ml.) was added concentrated hydrochloric acid (50 ml.). The solution was evaporated to dryness and the residue heated under reflux for 5 hours in n-butanol (250 ml.) with sodium dicyanamide (45 g.). The butanol solution was cooled to room temperature and filtered and the clear filtrate evaporated to dryness. The residue in water (200 ml.) was treated with concentrated hydrochloric acid (50 ml.) and thioacetamide (38 g.) and then heated on a steam-bath for 1 hour. The mixture was then cooled and extracted with ethyl acetate (200 ml.). The aqueous layer was separated, basified with aqueous sodium hydroxide to pH ~ 11 and extracted with ethyl acetate (200 ml.). The aqueous layer was separated and evaporated to dryness. The residue was purified by chromatography on silica gel using ethyl acetate/methanol/acetic acid 6:2:0.2 v/v/v and the appropriate fraction combined and evaporated to dryness.

A mixture of (2-hydroxyethyl)amidinothiourea (6.5 g.) and N-(6-chloro-5-oxohexyl)phthalimide (10 g.) was heated under reflux in ethanol (100 ml.) for 1 hour and the solution then evaporated to dryness. The residue was dissolved in water (100 ml.) and the pH adjusted to ~7 with dilute aqueous sodium hydroxide. The solution was then extracted with ethyl acetate (100 ml.), the organic layer was separated and evaporated to dryness. The residue in acetone was treated with maleic acid (3 g.) in acetone. The white product was filtered off and dried to give 4.6 g. of 2-[2-(2-hydroxyethyl)guanidino]-4-(4-phthalimidobutyl)thiazole 1.25 maleate.

A solution of 2-[2-(2-hydroxyethyl)guanidino]-4-(4-phthalimidobutyl)thiazole 1.25 maleate (4.4 g.) in ethanol/water (50 ml./50 ml.) containing sufficient aqueous sodium hydroxide to give a pH of 11 was heated under reflux for 15 minutes and the pH adjusted to 3 with concentrated hydrochloric acid. After heating under reflux for a further 15 minutes the solution was basified with aqueous sodium hydroxide and extracted with chloroform (50 ml.). The organic layer was separated, evaporated to dryness and the residue was recrystallised from acetonitrile to give 0.95 g. of 2-[2-(2-hydroxyethyl)guanidino]-4-(4-aminobutyl)thiazole.

EXAMPLE 5

A mixture of 2-[2-(2-methylthioethyl)guanidino]-4-(4-aminobutyl)thiazole (400 mg.) and dimethyl (cyanoimido)dithiocarbonate (200 mg.) in ethanol (30 ml.) was stirred at room temperature for 2 hours. The solution was then evaporated to dryness to give an oil (550 mg.). This was triturated with a small volume of ethanol to give 280 mg. of 2-[2-(2-methylthioethyl)guanidino]-4-[4-(3-cyano-2-methylisothioureido)butyl]-thiazole, m.p. 124°-6°.

The 2-[2-(2-methylthioethyl)guanidino]-4-(4-aminobutyl)thiazole used as starting material may be prepared as follows:

A mixture of 2-methylthioethylamine (3.4 g.), sodium dicyanamide (3.4 g.), concentrated hydrochloric acid (3.3 ml.) and n-butanol (40 ml.) was heated under reflux with stirring for 16 hours. Filtration of the mixture and evaporation of the filtrate gave crude (2-methylthioethyl)cyanoguanidine as a viscous oil (7.0 g.) (containing some butanol). This oil was heated on a steam bath with water (50 ml.), concentrated hydrochloric acid (3.3 ml.) and thioacetamide (2.8 g.) for two hours. The solution was cooled, basified with 10% w/v sodium hydroxide, and extracted with ethyl acetate. After drying (MgSO$_4$) and filtering the filtrate was evaporated to give a yellow oil. This was treated with one equivalent of maleic acid in acetone to give 4.9 g. of (2-methylthioethyl)amidinothiourea hydrogen maleate m.p. 139°–140°.

A solution of (2-methylthioethyl)amidinothiourea (prepared from the hydrogen maleate) (1.4 g.) and N-(6-chloro-5-oxohexyl)phthalimide (2.1 g.) in ethanol (30 ml.) was heated under reflux for 2 hours and then evaporated to dryness. On triturating the residue with acetone the product, 2-[2-(2-methylthioethyl)guanidino]-4-(4-phthalimidobutyl)thiazole hydrochloride, separated. This was filtered off and air dried (1.4 g.), m.p. 141°–2°.

This material was heated under reflux in a mixture of ethanol (10 ml.) and water (10 ml.) containing sufficient aqueous sodium hydroxide to give a pH of 11. After ten minutes the pH was adjusted to 3 with concentrated hydrochloric acid and maintained at this pH by occasional additions of concentrated hydrochloric acid. After 45 minutes the pH was adjusted to 11 with aqueous sodium hydroxide and the solution evaporated. The residue was extracted with methylene chloride, dried (MgSO$_4$), and evaporated to give 2-[2-(2-methylthioethyl)guanidino]-4-(4-aminobutyl)thiazole as a yellow oil which was used without further purification.

EXAMPLE 6

A solution of 2-[2-(2-methylthioethyl)guanidino]-4-[4-(3-cyano-2-methylisothioureido)butyl]thiazole (260 mg.) in 33% w/v ethanolic methylamine (20 ml.) was stirred at room temperature for 16 hours. The solution was evaporated to dryness and the residue dissolved in acetone. This solution was treated with one equivalent of maleic acid in acetone. The viscous oil obtained on evaporation gave on trituration with acetone, 250 mg. of 2-[2-(2-methylthioethyl)guanidino]-4-[4-(2-cyano-3-methylguanidino)butyl]thiazole hydrogen maleate, m.p. 76°–8° after recrystallisation from ethyl acetate/methanol.

EXAMPLE 7

A mixture of 2-[2-(2-methoxyethyl)guanidino]-4-[(2-aminoethyl)thiomethyl]thiazole (1.4 g.) and dimethyl (cyanoimido)dithiocarbonate (0.7 g.) in ethanol (10 ml.) was stirred overnight at room temperature. To the reaction mixture, containing 2-[2-methoxyethyl)guanidino]-4-[2-(3-cyano-2-methylisothioureido)ethylthiomethyl]thiazole, was then added 33% w/v ethanolic methylamine (40 ml.). After standing for 4 hours the mixture was evaporated to dryness and the residue, in acetone (100 ml.), was treated with fumaric acid (0.6 g.) in acetone. The solid precipitate was filtered off and dried to give 1.2 g. of 2-[2-(2-methoxyethyl)guanidino]-4-[2-(2-cyano-3-methylguanidino)ethylthiomethyl]thiazole fumarate, m.p. 174°–177° on recrystallisation from water (yield 58%).

The 2-[2-(2-methoxyethyl)guanidino]-4-[(2-aminoethyl)thiomethyl]thiazole used as starting material may be prepared as follows:

A mixture of (2-methoxyethyl)amidinothiourea (4.5 g.) and 1,3-dichloroacetone (3.3 g.) was stirred in acetone (50 ml.). After 3 hours concentrated hydrochloric acid (0.3 ml.) was added. The mixture was then allowed to stand at room temperature for 2 days. The precipitated white solid was filtered off and dried to give 4.9 g. of 2-[2-(2-methoxyethyl)guanidino]-4-chloromethylthiazole hydrochloride, m.p. 158°–160°.

To a mixture of 2-aminoethanethiol hydrochloride (3.8 g.) in ethanol (80 ml.) was added a solution of sodium hydroxide (2.1 g.) in water (15 ml.). To the resulting solution was added 2-[2-(2-methoxyethyl)guanidino]-4-chloromethylthiazole hydrochloride (4.8 g.) in ethanol (40 ml.). The mixture was stirred for 5 minutes and then a solution of sodium hydroxide (0.65 g.) in water (5 ml.) was added. After 1 hour the mixture was evaporated to dryness. The residue was partitioned between water (50 ml.) and ethyl acetate (2×50 ml.). The combined ethyl acetate layers were combined and evaporated to dryness to give 5 g. of 2-[2-(2-methoxyethyl)guanidino]-4-[(2-aminoethyl)thiomethyl]thiazole as a brown oil. A sample converted to the di(hydrogen maleate) had m.p. 136°–139°.

EXAMPLE 8

A mixture of 2-[2-(2-dimethylaminoethyl)guanidino]-4-(4-aminobutyl)thiazole (0.3 g.) and methylisothiocyanate (0.2 g.) in acetonitrile (2 ml.) was allowed to stand at room temperature for 18 hours. The mixture was then evaporated to dryness and the residue purified by medium pressure liquid chromatography using chloroform/methanol/concentrated aqueous ammonia (s.g. 0.880) 15:1:0.0.05 v/v/v as eluant. The appropriate fraction was evaporated to dryness and 2-[2-(2-dimethylaminoethyl)guanidino]-4-[4-(3-methyl)thioureido]thiazole obtained as a gum (0.18 g.). The nuclear magnetic resonance spectrum obtained in d$_6$-dimethyl sulphoxide contained the following resonances (δ): 1.5 (m,4H); 2.15 (s,6H); 2.4 (m,6H,includes DMSO); 2.75 (d,3H); 3.25 (m,10H, includes H$_2$O); 6.25 (s,1H); 6.95 (bs,1H); 7.3 (bs, 4H).

The 2-[2-(2-dimethylaminoethyl)guanidino]-4-[4-aminobutyl)thiazole used as starting material may be prepared as follows:

To 2-dimethylaminoethylamine (30 g.) in water (100 ml.) was added concentrated HCl (33 ml.). The solution was evaporated to dryness and the residue heated under reflux in butanol (200 ml.) with sodium dicyanamide (30 g.) for 5 hours. The cooled mixture was then filtered and evaporated to dryness. The residue was dissolved in water (200 ml) containing thioacetamide (25 g.) and concentrated HCl (66 ml.). The solution was heated at 90° C. for 2 hours, basified with sodium hydroxide and then evaporated to dryness. The residue was dissolved in acetone and treated with maleic acid to give 10 g. of (2-dimethylaminoethyl)amidinothiourea hydrogen maleate. A sample recrystallised from methanol had m.p. 142°–144° C.

A mixture of (2-dimethylaminoethyl)amidinothiourea (3.2 g.) and 6-phthalimido-1-chlorohexan-2-one (2.8 g.) was heated under reflux in ethanol (80 ml.) for 1 hour. The mixture was evaporated to dryness and the residue heated under reflux in a mixture of water (40 ml.) and ethanol (40 ml.) containing sufficient sodium hydroxide to give a pH of ~11. After 15 minutes the pH was adjusted to ~3 with concentrated HCl and the mixture heated under reflux for a further 30 minutes. The pH was then adjusted to 11 with sodium hydroxide and the mixture extracted with chloroform (3×50 ml.). The combined extracts were evaporated to dryness and the residue purified by medium pressure liquid chromatography using chloroform/methanol/concentrated aqueous ammonia (s.g. 0.880) 9:1:0.05 v/v/v as eluant. The appropriate fraction evaporated to dryness gave 1.4 g. of 2-[2-(2-dimethylaminoethyl)guanidino]-4-(4-aminobutyl)thiazole as a gum which was used without further purification.

EXAMPLE 9

A mixture of 2-[2-(2-methoxyethyl)guanidino]-4-[5-aminopentyl]thiazole (0.58 g.) and 1-methylthio-1-methylamino-2-nitroethylene (0.3 g.) in acetonitrile (5 ml.) was heated under reflux for 4 hours. The mixture was then evaporated to dryness and the residue purified by medium pressure liquid chromatography using a mixture of chloroform, methanol and concentrated aqueous ammonia (s.g. 0.880) as eluant. The appropriate fractions were evaporated to dryness and the residue was treated with fumaric acid in ethanol/acetone to give 0.39 g. of 1-[5-(2-[2-methoxyethyl]guanidinothiazol-4-yl)pentylamino]-1-methylamino-2-nitroethylene fumarate, m.p. 133°–136° C.

EXAMPLE 10

A mixture of 2-[2-(2-methoxyethyl)guanidino]-4-[5-aminopentyl]thiazole (0.58 g.) and dimethyl (cyanoimido)dithiocarbonate (0.3 g.) was heated under reflux in ethanol (5 ml.) until a clear solution resulted and then allowed to stand at room temperature for 4 hours. The mixture was then evaporated to dryness and the residue of 2-[2-(2-methoxyethyl)guanidino]-4-[5-(2-cyano-3-methylisothioureido)pentyl]thiazole was then dissolved in ethanolic methylamine (33% w/v, 15 ml.). After standing at room temperature for 18 hours, the mixture was evaporated to dryness and the residue treated in a mixture of ethanol and acetone with fumaric acid to give 0.6 g. of 2-[2-(2-methoxyethyl)guanidino]-4-[5-(2-cyano-3-methylguanidino)pentyl]thiazole fumarate, m.p. 184°–187° C.

The 2-[2-(2-methoxyethyl)guanidino]-4-[5-aminopentyl]thiazole used as starting material may be prepared as follows:

A mixture of (2-methoxyethyl)amidinothiourea (3 g.) and 7-phthalimido-1-chloroheptan-2-one (5 g.) in ethanol (100 ml.) was heated under reflux for 1 hour. The mixture was then evaporated to dryness. The residue was dissolved in ethyl acetate. On standing 6.5 g. of 2-[2-(2-methoxyethyl)guanidino]-4-(5-phthalimidopentyl)thiazole hydrochloride was precipitated. This material was heated under reflux in a mixture of ethanol (50 ml.) and water (50 ml.) and dilute sodium hydroxide added until the pH was approximately 11. After 15 minutes concentrated HCl was added to pH 3 and the mixture heated under reflux for 0.5 hours. The mixture was then evaporated to dryness and the residue extracted from aqueous NaOH with chloroform. The chloroform extracts were evaporated to dryness to yield a clear oil. A sample treated with fumaric acid in ethanol gave 2-[2-(2-methoxyethyl)guanidino]-4-(5-aminopentyl)thiazole 1.5 fumarate, m.p. 118°–121° C.

EXAMPLE 11

A mixture of 2-[2-(2-methoxyethyl)guanidino]-4-[5-aminopentyl]thiazole (0.29 g.) and acetic anhydride (0.12 g.) in acetonitrile (5 ml.) was heated at 50° C. for 3 hours. The mixture was evaporated to dryness and the residue treated with fumaric acid in a mixture of acetone and ethanol to give 0.18 g. of 2-[2-(2-methoxyethyl)guanidino]-4-[5-acetylaminopentyl]thiazole fumarate, m.p. 179°–182° C.

EXAMPLE 12

A mixture of 2-[2-(2-methoxyethyl)guanidino]-4-[5-aminopentyl]thiazole (0.29 g.) and ethyl N-cyanoacetimidate (0.13 g.) in acetonitrile (2 ml.) was allowed to stand at room temperature for 18 hours. The mixture was evaporated to dryness and the residue purified by medium pressure liquid chromatography using chloroform/methanol/concentrated aqueous ammonia (s.g. 0.880) 15:1:0.05 v/v/v as eluant. The appropriate fractions were evaporated to dryness and then treated with fumaric acid in a mixture of acetone and ethanol to give 0.17 g. of 2-[2-(2-methoxyethyl)guanidino]-4-[5-(2-cyano 3-methylamidino)pentyl]thiazole fumarate, m.p. 162°–164° C.

EXAMPLE 13

To 2-[4-(2-cyano-3-methylguanidino)butyl]-4-[2-(2-methoxyethyl)thioureido]pyrimidine (0.6 g.) in saturated methanolic ammonia (100 ml.) was added mercuric oxide (0.54 g.). The resulting suspension was stirred for 30 minutes and then filtered. The filtrate was evaporated to dryness and the residue triturated in ether to give 2-[4-(2-cyano-3-methylguanidino)butyl]-4-[2-(2-methoxyethyl)guanidino]pyrimidine (0.45 g.), m.p. 162°–165° C.

The 2-[4-(2-cyano-3-methylguanidino)butyl]-4-[2-(2-methoxyethyl)guanidino]pyrimidine used as starting material may be prepared as follows:

To a mixture of 5-phthalimidovaleronitrile (35.6 g.) and ethanol (8.2 g.) in tetrahydrofuran (150 ml.) cooled to 0° C. was added hydrogen chloride gas until the mixture was saturated. The mixture was allowed to stand at 0° C. for 24 hours and then evaporated to dryness. The residue was dissolved in ethanol (150 ml.) and a solution of sodium metal (3.6 g.) in ethanol (150 ml.) was added. Ammonium chloride (8.3 g.) was added and the mixture was stirred at room temperature for 2 days. The mixture was then evaporated to dryness and the residue triturated with acetonitrile. The solid product was filtered off and dissolved in a mixture of ethanol (100 ml.) and triethylamine (32 ml.) and 2-chloroacrylonitrile (11.1 ml.) added. The resulting mixture was stirred overnight at room temperature and then heated under reflux for 1 hour. The mixture was then evaporated to dryness and the residue partitioned between ethyl acetate and water. The organic layer was extracted with dilute aqueous acid and the aqueous solution basified with sodium bicarbonate and extracted with ethyl acetate. The organic layer was evaporated and the residue treated with excess maleic acid in ethyl acetate gave 2-[4-phthalimidobutyl)-4-aminopyrimidine hydrogen maleate (7.4 g.). The nuclear magnetic resonance spectrum in d$_6$-dimethylsulphoxide included the following resonances: 1.65 (m,4H); 2.7 (t,2H); 3.6 (t,2H); 6.03 (s,2H); 6.5 (d,1H); 7.8 (s,4H); 8.05 (d,1H); 8.4 (s,2H).

To 2-(4-phthalimidobutyl)-4-aminopyrimidine (2.0 g.) in acetonitrile (4 ml.) was added 2-methoxyethylisothiocyanate (2.0 g.). The resulting mixture was heated under reflux for 4 days, evaporated to dryness and the residue crystallised from acetonitrile to give 1.6 g. of 2-(4-phthalimidobutyl)-4-[3-(2-methoxyethyl)thiourido]pyrimidine, m.p. 166°–169° C.

To 2-(4-phthalimidobutyl)-4-[3-(2-methoxyethyl)thioureido]pyrimidine (1.6 g.) in a mixture of ethanol (50 ml.) and water (50 ml.) was added dilute aqueous sodium hydroxide until a pH of 11 was obtained. The resulting mixture was heated on a steam-bath for 15 minutes. The mixture was then acidified with aqueous HCl to pH 3 and heated a further 15 minutes. The mixture was then cooled to room temperature and the pH adjusted to 11 with dilute aqueous sodium hydoxide and the mixture extracted with chlorform. The organic layer was evaporated to give 1.04 g. of 2-[4-aminobutyl]-4-[3-(2-methoxyethyl)thioureido]-pyrimidine. The fumarate of this compound had m.p. 178°–180° C.

To 2-(4-aminobutyl)-4-[3-(2-methoxyethyl)thioureido]pyrimidine (1 g.) was added dimethyl (cyanoimino)dithiocarbonate (0.5 g.) in ethanol (20 ml.). The mixture was stirred for 30 minutes and then the precipitated solid was filtered off and dissolved in ethanolic methylamine (33% w/v; 50 ml.). The resulting solution was allowed to stand for 18 hours and then evaporated to dryness. The resulting gum crystallised on standing and was triturated with ether to give 0.64 g. of 2-[4-(2-cyano-3-methylguanidino)butyl]-4-[3-(2-methoxyethyl)thioureido]pyrimidine. The nuclear magnetic resonance spectrum in d$_6$-dimethylsulphoxide contained the following resonances: 1.7 (m,4H); 2.75 (d,3H); 2.85 (t,2H); 3.2 (t,obscured by water); 3.4 (s,3H); 3.8 (m,4H); 6.7 (s,2H); 7.0 (d,1H); 8.45 (d,1H); 10.75 (s,1H).

We claim:

1. A guanidine derivative of the formula:

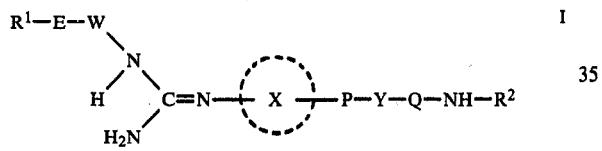

in which

W is a straight chain 2–6C alkylene chain optionally substituted by one or two 1–4C alkyl radicals;

E is an oxygen or sulphur atom, a sulphinyl or sulphonyl radical, or a radical of the formula NR$^3$ in which R$^3$ is a hydrogen atom or a 1–6C alkyl radical;

R$^1$ is a hydrogen atom or a straight-chain 1–6C alkyl radical optionally substituted by one or two 1–4C alkyl radicals; or R$^1$ and R$^3$ are alkyl and are joined to form, together with the nitrogen atoms to which they are attached, a morpholine, pyrrolidine, piperidine or piperazine ring;

ring X is a phenyl ring carrying 1 or 2 optional substituents or a 5- or 6-membered heterocyclic aromatic ring selected from the group consisting of a thiophene, pyridine, pyrimidine, imidazole, thiazole, oxazole, pyrazole, triazole, thiadiazole, oxadiazole, pyrazine, pyridazine, isothiazole, isoxazole or triazine ring, which heterocyclic ring may, where possible, carry a single optional substituent, the optional substituents on ring X being selected from fluorine, chlorine, bromine and iodine atoms and 1–6C alkyl, 1–6C alkoxy, 1–6C alkylthio, trifluoromethyl, hydroxy and amino radicals;

Y is an oxygen or sulphur atom, a direct bond, a methylene, cis or trans vinylene or sulphinyl radical or a radical of the formula NR$^4$ in which R$^4$ is a hydrogen atom or a 1–6C alkyl radical;

P is a direct bond or a 1–4C unbranched alkylene radical optionally substituted by one or two 1–4C alkyl radicals;

Q is a 1–4C unbranched alkylene radical optionally substituted by one or two 1–4C alkyl radicals, provided that when Y is an oxygen atom, a sulphinyl radical or a radical of the formula NR$^4$, Q is a 2–4C optionally substituted alkylene radical;

R$^2$ is a radical of the formula —A—B in which A is a 3,4-dioxocyclobuten-1,2-diyl radical or a radical of the formula C=Z in which Z is a sulphur or oxygen atom or a radical of the formula NCN, NNO$_2$, CHNO$_2$, NCONH$_2$, C(CN)$_2$, NCOR$^5$, NSO$_2$R$^5$, NCO$_2$R$^5$ or NR$^6$ in which R$^5$ is a 1–6C alkyl, 1–6C haloalkyl, 7–10C alkylaryl or 6–10C aryl radical or a pyridyl radical and R$^6$ is a hydrogen atom or a 1–6C alkyl, 1–6C haloalkyl, 7–10C alkylaryl or 6–10C aryl radical or —A— is a radical of the formula:

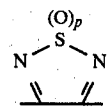

II in which p is 1 or 2 and B is a 1–6C alkyl, 1–6C alkoxy or 1–6C alkylthio radical or a radical of the formula NR$^7$R$^8$ in which R$^7$ and R$^8$, which may be the same or different, are hydrogen atoms or 1–6C alkyl, 1–6C haloalkyl, 2–6C alkoxycarbonyl, 3–6C alkenyl, 3–6C alkynyl (in which the double or triple bond respectively is separated from the nitrogen atom or NR$^7$R$^8$ by at least one carbon atoms), 2–6C (primary hydroxy)alkyl, 2–6C (primary amino)alkyl, 3–8C alkylaminoalkyl, 4–8C dialkylaminoalkyl (in the latter two of which the nitrogen atom is separated from the nitrogen atom of NR$^7$R$^8$ by at least two carbon atoms), 6–10C aryl or 3–8C cycloalkyl radicals, or R$^7$ and R$^8$ are alkyl and are joined to form, together with the nitrogen atom to which they are attached, a 5- or 6-membered saturated ring which optionally contains an oxygen atom or an NR$^9$ radical in which R$^9$ is a hydrogen atom or a 1–6C alkyl radical;

and the pharmaceutically-acceptable acid-addition salts thereof.

2. A guanidine derivative as claimed in claim 1 in which

W is a 2–6C alkylene chain optionally substituted by one or two methyl radicals;

E is an oxygen or sulphur atom, a sulphinyl or sulphonyl radical or a radical of the formula NR$^3$ in which R$^3$ is a hydrogen atom or a methyl radical;

R$^1$ is a hydrogen atom or a methyl radical or R$^1$ and R$^3$ are joined to form, together with the nitrogen atom to which they are attached, a morpholine or piperidine ring;

ring X is a phenyl, thiophene, pyridine, pyrimidine, imidazole, thiazole, oxazole, pyrazole, triazole, thiadiazole, oxadiazole, pyrazine, pyridazine, isothiazole, isoxazole, or triazine ring, each of which is optionally substituted, where possible, by a fluorine, chlorine, bromine or iodine atom or by a methyl, methoxy, methylthio, trifluoromethyl, hydroxy or amino radical;

R$^4$ is a hydrogen atom or a methyl radical;

P is a direct bond or a 1–4C unbranched alkylene radical optionally substituted by a methyl radical;

Q is a 1–4C unbranched alkylene radical optionally substituted by a methyl radical;

$R^5$ is a methyl, ethyl, n-propyl, i-propyl, n-butyl, trifluoromethyl, 2,2,2-trifluoroethyl, phenyl, p-tolyl or pyridyl radical;

$R^6$ is a hydrogen atom or a methyl, 2,2,2-trifluoroethyl, phenyl or p-tolyl radical;

B is a methyl, ethyl, methoxy, ethoxy or methylthio radical or a radical of the formula $NR^7R^8$ in which $R^7$ and $R^8$, which may be the same or different, are hydrogen atoms or methyl, ethyl, i-propyl, 2,2,2-trifluoroethyl, methoxycarbonyl, ethoxycarbonyl, allyl, propargyl, 2-hydroxyethyl, 2-aminoethyl, 2-methylaminoethyl, 2-dimethylaminoethyl, 2-diethylaminoethyl, cyclohexyl or phenyl radicals or $R^7$ and $R^8$ are joined to form a pyrrolidine, piperidine, morpholine, piperazine or N-methylpiperazine ring.

3. A guanidine derivative as claimed in claim 1 or claim 2 in which $R^1$ is an optionally-substituted alkyl radical and E is an oxygen or sulphur atom.

4. A guanidine derivative as claimed in any of claims 1 to 2 in which —$R^2$ is a radical of the formula —A—B in which A is a radical of the formula C=Z in which Z is a radical of the formula NCN, $CHNO_2$ or $NSO_2R^5$ and B is a radical of the formula $NHR^7$.

5. A guanidine derivative selected from the group consisting of

2-[2-(2-methoxyethyl)guanidino]-4-[4-(2-cyano-3-methylguanidino)butyl]thiazole;

2-[2-(2-methoxyethyl)guanidino]-4-[4-(2-methylsulphonyl-3-methylguanidino)butyl]thiazole;

2-[2-(2-methylthioethyl)guanidino]-4-[4-(2-cyano-3-methylguanidino)butyl]thiazole;

1-[5-(2-[2-methoxyethyl]guanidinothiazol-4-yl)pentylamino]-1-methylamino-2-nitroethylene;

2-[2-(2-methoxyethyl)guanidino]-4-[5-(2-cyano-3-methylguanidino)pentyl]thiazole;

2-[4-(2-cyano-3-methylguanidino)butyl]-4-[2-(2-methoxyethyl)guanidino]pyrimidine;

and the pharmaceutically-acceptable acid-addition salts thereof.

6. A guanidine derivative as claimed in any of claims 1 to 2 in which —$R^2$ is a radical of the formula —A—B in which A is a radical of the formula II and B is a radical of the formula $NHR^7$.

7. A pharmaceutical composition comprising a guanidine derivative as claimed in claim 1 in an amount effective to inhibit the secretion of gastric acid in a warm-blooded animal in association with a non-toxic pharmaceutically-acceptable diluent or carrier.

8. A method of inhibiting gastric acid secretion in a living animal comprising administering to the animal a composition of claim 7.

* * * * *